US009174907B2

(12) United States Patent
Brammer et al.

(10) Patent No.: US 9,174,907 B2
(45) Date of Patent: Nov. 3, 2015

(54) HYDROFORMYLATION PROCESS

(71) Applicant: Dow Technology Investments LLC, Midland, MI (US)

(72) Inventors: Michael A. Brammer, Lake Jackson, TX (US); Rick B. Watson, Missouri City, TX (US); Avery L. Watkins, Pearland, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/398,804

(22) PCT Filed: May 22, 2013

(86) PCT No.: PCT/US2013/042134
§ 371 (c)(1),
(2) Date: Nov. 4, 2014

(87) PCT Pub. No.: WO2013/184350
PCT Pub. Date: Dec. 12, 2013

(65) Prior Publication Data
US 2015/0133695 A1    May 14, 2015

Related U.S. Application Data

(60) Provisional application No. 61/655,183, filed on Jun. 4, 2012.

(51) Int. Cl.
*C07C 45/50* (2006.01)
*B01J 31/24* (2006.01)
*B01J 31/40* (2006.01)

(52) U.S. Cl.
CPC .............. *C07C 45/50* (2013.01); *B01J 31/24* (2013.01); *B01J 31/4038* (2013.01); *B01J 31/4046* (2013.01); *B01J 31/4053* (2013.01); *B01J 2531/80* (2013.01)

(58) Field of Classification Search
CPC ...................................................... C07C 45/50
USPC ....................................................... 568/454
See application file for complete search history.

(56) References Cited

U.S. PATENT DOCUMENTS

| | | |
|---|---|---|
| 3,415,906 A | 12/1968 | Shepard et al. |
| 3,527,809 A | 9/1970 | Pruett et al. |
| 4,148,830 A | 4/1979 | Pruett et al. |
| 4,221,743 A | 9/1980 | Halstead et al. |
| 4,247,486 A | 1/1981 | Brewester et al. |
| 4,283,304 A * | 8/1981 | Bryant et al. ............. 502/24 |
| 4,518,809 A | 5/1985 | Forster et al. |
| 4,528,403 A | 7/1985 | Tano et al. |
| 4,567,302 A | 1/1986 | Sivaramakrishnan |
| 4,567,306 A | 1/1986 | Dennis et al. |
| 4,593,127 A | 6/1986 | Buning et al. |
| 4,599,206 A | 7/1986 | Billig et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,861,918 A | 8/1989 | Miller et al. |
| 4,885,401 A | 12/1989 | Billig et al. |
| 5,102,505 A | 4/1992 | Sorensen |
| 5,110,990 A | 5/1992 | Blessing et al. |
| 5,113,022 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,288,918 A | 2/1994 | Maher et al. |
| 5,312,996 A | 5/1994 | Packett |
| 5,360,938 A | 11/1994 | Babin et al. |
| 5,364,950 A | 11/1994 | Babin et al. |
| 5,391,801 A | 2/1995 | Sato et al. |
| 5,430,194 A | 7/1995 | Bazner et al. |
| 5,466,644 A * | 11/1995 | Konkol et al. ............. 502/28 |
| 5,491,266 A | 2/1996 | Babin et al. |
| 5,527,950 A | 6/1996 | Hansen et al. |
| 5,675,041 A | 10/1997 | Kiss et al. |
| 5,681,473 A | 10/1997 | Miller et al. |
| 5,710,344 A | 1/1998 | Breikss et al. |
| 5,728,893 A | 3/1998 | Becker et al. |
| 5,731,472 A | 3/1998 | Leung et al. |
| 5,741,944 A * | 4/1998 | Bryant et al. ............. 568/454 |

(Continued)

FOREIGN PATENT DOCUMENTS

| | | |
|---|---|---|
| CN | 1986055 | 6/2007 |
| EP | 306094 | 1/1992 |

(Continued)

OTHER PUBLICATIONS

CRC Handbook of Chemistry and Physics, 72nd Ed. (1991-1992), CRC Press, p. 1-10.

(Continued)

*Primary Examiner* — Sikarl Witherspoon

(57) ABSTRACT

A process comprising contacting a reaction fluid, which contains at least one phosphorus acidic compound, with a buffer solution to neutralize at least some amount of the phosphorus acidic compound, wherein the buffer solution comprises at least one salt of an unsaturated aliphatic carboxylic acid.

9 Claims, No Drawings

(56) References Cited

U.S. PATENT DOCUMENTS

| | | |
|---|---|---|
| 5,744,649 A | 4/1998 | Bryant et al. |
| 5,874,640 A | 2/1999 | Bryant et al. |
| 5,886,235 A | 3/1999 | Bryant et al. |
| 5,892,119 A | 4/1999 | Bryant et al. |
| 5,917,095 A | 6/1999 | Bryant et al. |
| 5,929,289 A | 7/1999 | Abatjoglou et al. |
| 6,153,800 A | 11/2000 | Gelling et al. |
| 6,265,620 B1 | 7/2001 | Urata et al. |
| 6,440,891 B1 | 8/2002 | Maas et al. |
| 7,009,068 B2 | 3/2006 | Schmutzler et al. |
| 7,145,042 B2 | 12/2006 | Volland et al. |
| 7,196,230 B2 | 3/2007 | Peng et al. |
| 7,550,406 B2 | 6/2009 | Jeon et al. |
| 7,586,010 B2 | 9/2009 | Liu et al. |
| 7,615,645 B2 | 11/2009 | Volland et al. |
| 7,674,937 B2 | 3/2010 | Tolleson et al. |
| 7,872,156 B2 | 1/2011 | Liu et al. |
| 8,003,816 B2 | 8/2011 | Selent et al. |
| 8,884,072 B2 | 11/2014 | Miller et al. |
| 2008/0188686 A1 | 8/2008 | Hess et al. |
| 2010/0069679 A1 | 3/2010 | Puckette |
| 2011/0028746 A1 | 2/2011 | Rudolph et al. |

FOREIGN PATENT DOCUMENTS

| | | |
|---|---|---|
| GB | 1497627 | 1/1978 |
| WO | 8808835 | 11/1988 |

OTHER PUBLICATIONS

Feldman, et al., "Membrane-supported rhodium hydroformylation catalysts", Journal of Molecular Catalysis, 1990, 63, p. 213-221.

Jongsma, et al., "Fine tuning of bulky-phosphite modified rhodium catalysts by binding them to copolymers", Journal of Molecular Catalysis, 1993, 83, p. 17-35.

Chemtech, 13, 1983.

Parrinello, et al., "Asymmetric Hydroformylation Catalyzed by Homogeneous and Polymer-Supported Platinum Complexes Containing Chiral Phosphine Ligands", Journal American Chemical Society, 1987, 109, p. 7122-7127.

Mata-Perez, et al., "The Kinetic Rate Law for Autocatalytic Reactions", Journal of Chemical Education, vol. 64, No. 11, Nov. 1987, p. 925-927.

\* cited by examiner

HYDROFORMYLATION PROCESS

CROSS-REFERENCE TO RELATED APPLICATIONS

This application claims priority from provisional application Ser. No. 61/655,183, filed Jun. 4, 2012, which is incorporated herein by reference in its entirety.

BACKGROUND OF THE INVENTION

This invention relates to hydroformylation processes. In one aspect, the invention relates to a process for the mitigation of catalyst inhibition and ligand degradation.

In the rhodium/phosphite-catalyzed hydroformylation of olefins, the hydrolyzable ligand slowly and inexorably degrades to a number of by-products. Some of these by-products are acidic, and may be removed by contacting the reaction solution with an aqueous buffer (e.g. sodium phosphate). The resulting metal salts are appreciably soluble in water, and can be effectively removed, e.g. by extraction, from the organic phase. This extraction process is described in U.S. Pat. No. 5,741,944.

An additional problem inherent to rhodium-phosphite hydroformylation processes involves a loss of catalytic activity due to the formation of a class of diorganophosphite by-products. These compounds can coordinate to the active rhodium-phosphite catalyst and form new complexes that are less reactive. Fortunately, these diorganophosphite by-products may be preferentially hydrolyzed by contacting them with a buffer as described in U.S. Pat. No. 5,741,944.

Phosphate salts are recognized in the art as being preferred buffers. However, environmental agencies in some geographies have placed strict limits on the phosphorous content of plant effluent streams.

The preferred pH range of the aqueous buffer employed in U.S. Pat. No. 5,741,944 is 6-8. One set of phosphorous-free, buffer salts that buffer in this range are the maleates and fumarates. However, it has been reported that some $\alpha,\beta$-unsaturated carbonyls are catalyst inhibitors (see U.S. Pat. No. 4,861,918, U.S. Pat. No. 4,221,743 and EP 0 306 094 B1). Since these species can coordinate to rhodium in a bidentate fashion via their olefin and carbonyl moieties, it is generally believed that they inhibit the reaction by forming inactive complexes until such time as they are slowly reacted off the catalyst and the active site is thus made available for reaction. For example, hydroformylating acetylene gives acrolein, an $\alpha,\beta$-unsaturated aldehyde product that inhibits the catalyst until it is subsequently hydrogenated or hydroformylated to a bis-aldehyde (see U.S. Pat. No. 5,675,041 and WO 2010/030339). In another example, U.S. 2011/0028746 describes this type of interaction in a Rh-catalyzed decarboxylative hydroformylation, wherein extremely high concentrations of Rh (4600 ppm) were required. A list of expected rhodium hydroformylation poisons was tested in GB 1,497,627.

U.S. Pat. No. 5,466,644 and U.S. Pat. No. 4,283,304 teach the addition of maleic acid to destroy phosphorous-based ligands via a Michael addition reaction. In particular, '304 teaches that washing out any residual maleic acid is desirable, especially for commercial operations. Based on these two patents, a continuous extractor process, which would be expected to have traces of maleate going into the reaction system, would be expected to significantly impact ligand degradation via the Michael addition reaction. In systems with expensive ligands, increased ligand decomposition is not commercially acceptable.

It would be desirable to have an effective non-phosphorous based buffer that buffers in the range of pH 6 to 8 and is not detrimental to the hydroformylation process.

SUMMARY OF THE INVENTION

The invention includes a process comprising contacting a reaction fluid containing (a) a phosphorus acidic compound, (b) a metal-organophosphorus ligand complex catalyst that comprises a metal of Group 8, 9 or 10 complexed with an organophosphorous ligand, and, optionally, (c) free organophosphorus ligand, with an aqueous buffer solution to neutralize at least some amount of the phosphorus acidic compound of said reaction fluid to form a neutralized phosphorus acidic compound, wherein the buffer solution comprises a salt of an unsaturated aliphatic carboxylic acid.

Surprisingly, the buffer of the invention effectively removes the acidic by-products of phosphite ligand degradation and promotes the preferential hydrolysis of diorganophosphite by-products without substantially negatively impacting the hydroformylation process.

DETAILED DESCRIPTION OF THE INVENTION

The disclosed process involves treating the reaction fluid of a hydroformylation reaction with an aqueous buffer solution to neutralize at least some amount of one or more phosphorus acidic compounds from said reaction fluid. The hydroformylation process comprises contacting CO, $H_2$, and at least one olefin to form at least one aldehyde product in the presence of a catalyst comprising, a transition metal and an organophosphorous ligand. An amine and/or water are optionally employed in the hydroformylation process.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

As used herein, the term "heavies" means higher boiling aldehyde liquid condensation by-products.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and non-aromatic organic compounds, which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and non-aromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to 20 or more, preferably from 1 to 12. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction, which may be homogeneous or heterogeneous, and which compounds include those adhered to process equipment surfaces. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

The organophosphorous ligand comprises a hydrolysable phosphorous ligand (defined below) and may include mixtures thereof and may contain non-hydrolysable ligands, such as phosphines and the like.

"Hydrolysable phosphorous ligands" are trivalent phosphorous ligands that contain at least one P—Z bond wherein Z is oxygen, nitrogen, chloride, fluoride or bromide. Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—Z moieties such as polyphosphites, polyphosphoramidites, etc. and mixed P—Z moieties such as phosphite-phosphoramidites, fluorophosphite-phosphites, and the like.

In one embodiment, the invention is an extraction process for removing acidic impurities from a catalyst solution. Advantageously, the solution may be returned to a reaction zone of a hydroformylation process. The extraction process advantageously employs an aqueous buffer solution containing a metal salt of a carboxylic acid that contains an olefinic double bond. The pH of this aqueous solution advantageously is in the range of 6-8 and the solution is capable of substantial buffering capacity within this range. The catalyst solution advantageously comprises an organophosphorous ligand and a metal-organophosphorous ligand complex, and the extraction process comprises the step of contacting the catalyst solution with an aqueous buffer solution within an extraction zone of the hydroformylation process. The extraction zone is located after the reaction zone. In one embodiment of the invention, a vaporizer follows the reaction zone to vaporize volatile components of the liquid effluent stream of the reaction zone. Any non-vaporized liquid is sent to the extraction zone. The aqueous buffer solution advantageously is used to stabilize (1) the organophosphorous ligand against hydrolytic degradation and (2) the metal-organophosphorous ligand complex against degradation or deactivation, and (3) to remove or reduce the degradation products from the catalyst solution.

Illustrative metal-organophosphorous ligand complex catalyzed hydroformylation processes that may experience hydrolytic degradation include those processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; 5,491,266 and 7,196,230. P—Z containing species that will likely undergo hydrolytic degradation include organophosphonites, phosphoramidites, fluorophosphonites, and the like such as described WO 2008/071508, WO 2005/042458, and U.S. Pat. Nos. 5,710,344, 6,265,620, 6,440,891, 7,009,068, 7,145,042, 7,586,010, 7,674,937, and 7,872,156. These species will generate a variety of acidic and/or polar degradation products that can be extracted by use of the extractor technology taught in U.S. Pat. Nos. 5,744,649 and 5,741,944. Accordingly, the hydroformylation processing techniques that are advantageously employed with the invention disclosed herein may correspond to any known processing techniques. Preferred hydroformylation processes are those involving catalyst liquid recycle.

The substituted or unsubstituted olefinic unsaturated starting material reactants that may be employed in the hydroformylation processes of this invention include both optically active (prochiral and chiral) and non-optically active (achiral) olefinic unsaturated compounds containing from 2 to 40, preferably 3 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403). Moreover, such olefin compounds may further contain one or more additional ethylenic unsaturated groups, and of course, mixtures of two or more different olefinic unsaturated compounds may be employed as the starting hydroformylation material if desired. For example, commercial alpha olefins containing four or more carbon atoms may contain minor amounts of corresponding internal olefins and/or their corresponding saturated hydrocarbon and that such commercial olefins need not necessarily be purified from same prior to being hydroformylated. Illustrative mixtures of olefinic starting materials that can be employed in the hydroformylation reactions include, for example, mixed butenes, e.g., Raffinate I and II. Further such olefinic unsaturated compounds and the corresponding aldehyde products derived therefrom may also contain one or more groups or substituents that do not unduly adversely affect the hydroformylation process or the process of this invention such as described, for example, in U.S. Pat. Nos. 3,527,809 and 4,769,498.

Most preferably, the subject invention is especially useful for the production of non-optically active aldehydes, by hydroformylating achiral alpha-olefins containing from 2 to 30, preferably 3 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, 3-cyclohexyl-1-butene, and the like, as well as, 1,3-dienes, butadiene, alkyl alkenoates, e.g., methyl pentenoate, alkenyl alkanoates, alkenyl alkyl ethers, alkenols, e.g., pentenols, alkenals, e.g., pentenals, and the like, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, linalool, and the like.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. In general, with regard to the production of achiral (non-optically active) aldehydes, it is preferred to employ aldehyde compounds corresponding to the aldehyde products desired to be produced and/or higher boiling aldehyde liquid condensation by-products as the main organic solvents as is common in the art. Such aldehyde condensation by-products can also be preformed if desired and used accordingly. Illustrative preferred solvents employable in the production of aldehydes include ketones (e.g. acetone and methylethyl ketone), esters (e.g. ethyl acetate), di-2-ethylhexyl phthalate, 2,2,4-trimethyl-1,3-pentanediol monoisobutyrate), hydrocarbons (e.g. toluene), nitrohydrocarbons (e.g. nitrobenzene), ethers (e.g. tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. 4,148,830 and U.S. Pat. No. 4,247,486. Indeed, while one may employ, if desired, any suitable solvent at the start-up of a continuous process, the primary solvent will normally eventually comprise both aldehyde products and heavies, due to the nature of the continuous process. The amount of solvent is not especially critical and need only be sufficient to provide the reaction medium with the desired amount of transition metal concentration. Mixtures of two or more solvents may be employed.

Illustrative metal-organophosphorous ligand complexes employable in such hydroformylation reactions encompassed by this invention include the metal-organophosphorous ligand complex catalysts well known in the art, and include those disclosed in the patents mentioned above. In general, such catalysts may be preformed or formed in situ as described in such references and consist essentially of metal in complex combination with an organophosphorous ligand.

The permissible metals that make up the metal-organophosphorous ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium.

The term "complex" as used herein and in the claims means a coordination compound formed by the union of one or more electronically rich molecules or atoms capable of independent existence with one or more electronically poor molecules or atoms, each of which is also capable of independent existence. For example, the organophosphorous ligands employable herein may possess one or more phosphorus donor atoms, each having one available or unshared pair of electrons that are each capable of forming a coordinate covalent bond independently or possibly in concert (e.g., via chelation) with the metal. Carbon monoxide, which is also properly classified as a ligand, can also be present and complexed with the metal. The ultimate composition of the complex catalyst may also contain an additional ligand, e.g., hydrogen or an anion satisfying the coordination sites or nuclear charge of the metal.

The organophosphorous ligands that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are monoorganophosphite, diorganophosphite, triorganophosphite and organopolyphosphite compounds. Such organophosphorous ligands employable in this invention and/or methods for their preparation are well known in the art.

Representative monoorganophosphites may include those having the formula:

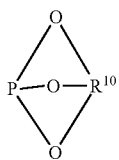

<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306.

Representative diorganophosphites may include those having the formula:

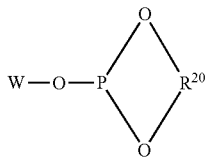

<<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302. More preferably $R^{20}$ is a divalent aromatic radical such as disclosed more fully, for example, in U.S. Pat. Nos. 4,599,206, 4,717,775, and 4,835,299.

Representative of a more preferred class of diorganophosphites are those of the formula:

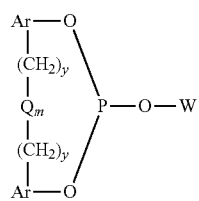

<<III>> wherein W is as defined above, each Ar is the same or different and represents a substituted or unsubstituted aryl radical, each y is the same or different and is a value of 0 or 1, Q represents a divalent bridging group selected from —$C(R^{33})_2$—, —O—, —S—, —$NR^{24}$—, $Si(R^{35})_2$— and —CO—, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

<<IV>> wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Such triorganophosphites are described in greater detail, for example, in U.S. Pat. Nos. 3,527,809 and 4,717,775.

Representative organopolyphosphites contain two or more tertiary (trivalent) phosphorus atoms and may include those having the formula:

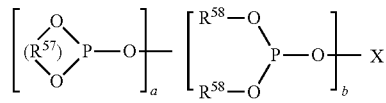

<<V>> wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^{57}$ radical may be the same or different. Each $R^{58}$ radical may also be the same or different.

Representative n-valent (preferably divalent) organic bridging radicals represented by X and representative divalent organic radicals represented by $R^{57}$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, and the like, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498; 4,774,361: 4,885,401; 5,113,022; 5,179,055; 5,202,297; 5,235,113; 5,264,616 and 5,364,950, and 5,527, 950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

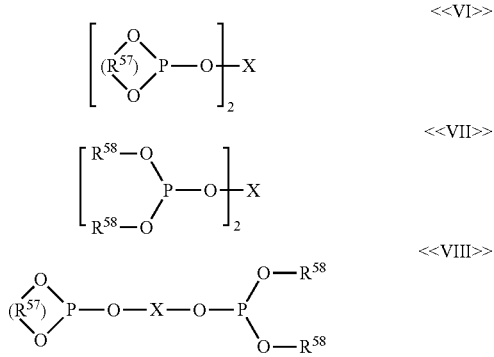

wherein each $R^{57}$, $R^{58}$ and X of Formulas (VI) to (VIII) are the same as defined above for Formula (V). Organophosphite ligands of such Formulas (V) to (VIII) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801.

Any of the $R^{11}$, $R^{20}$, $R^{46}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Any of the substituted or unsubstituted hydrocarbon radicals groups that make up a particular given organophosphite may be the same or different.

As noted above, the metal-organophosphorous ligand complex catalysts employable in this invention may be formed by methods known in the art. The metal-organophosphorous ligand complex catalysts may be in homogeneous or heterogeneous form. In any event, it is sufficient for the purpose of this invention that carbon monoxide, hydrogen and organophosphorous ligand compound are all ligands that are capable of being complexed with the metal and that an active metal-organophosphorous ligand catalyst is present in the reaction mixture under the conditions used in the hydroformylation reaction.

As noted, the hydroformylation processes of this invention involve the use of a metal-organophosphorous ligand complex catalyst as described herein. Mixtures of such catalysts can be employed if desired. The amount of metal-organophosphorous ligand complex catalyst present in the reaction fluid of a given hydroformylation process encompassed by this invention need only be that minimum amount necessary to provide the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above as employable herein. It is preferred that the free organophosphorous ligand be the same as the organophosphorous ligand of the metal-organophosphorous ligand complex catalyst employed. However, such ligands need not be the same in any given process. The hydroformylation process of this invention may involve from 0.1 moles or less to 100 moles or higher of free organophosphorous ligand per mole of metal in the reaction medium. The hydroformylation process of this invention preferably is carried out in the presence of from 1 to 50 moles of organophosphorous ligand and, more preferably, for organopolyphosphites from 1.1 to 4 moles of organopolyphosphite ligand per mole of metal present in the reaction medium; said amounts of organophosphorous ligand being the sum of both the amount of organophosphorous ligand that is bound (complexed) to the metal present and the amount of free (non-complexed) organophosphorous ligand present. Since it is more preferred to produce non-optically active aldehydes by hydroformylating achiral olefins, the more preferred organophosphorous ligands are achiral type organophosphorous ligands, especially those encompassed by Formula (V) above, and more preferably those of Formulas (VI), (VII) and (VII) above. Of course, if desired, make-up or additional organophosphorous ligand can be supplied to the reaction medium of the hydroformylation process at any time and in any suitable manner, e.g. to maintain a predetermined level of free ligand in the reaction medium.

As indicated above, the hydroformylation catalyst may be in heterogeneous form during the reaction and/or during the product separation. For example, the rhodium catalyst may be attached to a support so that the catalyst retains its solid form during both the hydroformylation and separation stages, or is soluble in a liquid reaction medium at high temperatures and then is precipitated on cooling. The rhodium catalyst may be attached to a thin film or membrane support, such as cellulose acetate or polyphenylenesulfone, as described in, for example, *J. Mol. Cat.*, 1990, 63, 213-221.

The metal, e.g., rhodium, catalyst may be attached to an insoluble polymeric support through an organophosphorus-containing ligand, such as a phosphite, incorporated into the polymer. The supported catalyst is not limited by the choice of polymer or phosphorus-containing species incorporated into it. Descriptions of polymer-supported catalysts may be found in for example: *J. Mol. Cat.*, 1993, 83, 17-35; Lieto, J. et al, *Chemtech* 13, 46(1983); *J. Am. Chem. Soc.*, 1987, 109, 7122-7127.

Extraction Process:

At least a portion of a reaction fluid obtained from a hydroformylation process advantageously is contacted with an aqueous buffer solution. Hydrolytic decomposition and rhodium catalyst deactivation can be prevented or lessened by treating at least a portion of the reaction fluid with the buffer solution when the fluid contains phosphorus acidic compounds formed during the hydroformylation process. In one embodiment of the invention, the fluid and buffer solution are contacted in an extraction zone under conditions sufficient to neutralize and remove at least some amount of the phosphorus acidic compounds from the reaction fluid. Following contact with the aqueous buffer, the organic phase can be returned to the reactor system.

It has been found that buffers derived from the metal salts of aliphatic carboxylic acids that contain an olefinic double bond are effective buffers when dissolved in water. Examples of said carboxylic acids are represented by the formula:

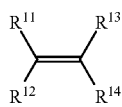

wherein $R^{11}$-$R^{14}$ are hydrogen, —COOM, alkyl, cycloalkyl, aryl, alkaryl and aralkyl radicals that may contain from 1 to 24 carbon atoms (and may form rings between themselves), and wherein at least one of $R^{11}$, $R^{12}$, $R^{13}$ and $R^{14}$ is a —COOM moiety, and M is a Group 1 or 2 metal (Na, K, Ca, etc.), or mixtures thereof. Preferably, at least one of $R^{11}$ and $R^{12}$ is a —COOM moiety and at least one of $R^{13}$ and $R^{14}$ is a —COOM moiety. In one embodiment of the invention, the acid is a dicarboxylic acid.

The amount of aqueous buffer solution employed, and time of contact with the reaction fluid, need only be that which is sufficient to neutralize at least some amount of the phosphorus acidic compounds that cause hydrolytic degradation of the desirable organophosphorous ligands. Preferably the amount of aqueous buffer solution is sufficient to at least maintain the concentration of such acidic compounds below the threshold level that causes substantial degradation of the hydrolysable organophosphorous ligand. For instance, a preferred quantity of aqueous buffer solution is a quantity that ensures that any degradation of the organophosphorous ligand proceeds by the "non-catalytic mechanism" as described in "The Kinetic Rate Law for Autocatalytic Reactions" by Mata-Perez et al., *Journal of Chemical Education*, Vol. 64, No. 11, November 1987, pages 925 to 927, rather than by the "catalytic mechanism" described in said article. The amount of buffer correlates with buffer capacity or the amount of acid species that can be removed without significant change in the extraction fluid pH. The concentration of the unsaturated organic acid salt buffer is not narrowly critical. Advantageously, the concentration of the buffer salt in the buffer solution is from 0.001M to 0.8M and more preferably is from 0.01 to 0.04M. In one embodiment of the invention, the maximum aqueous buffer solution concentration is governed by practical considerations. The preparation of buffers is well known in the art. Advantageously, degassed ($O_2$-free) de-ionized water is employed in the preparation of the buffer solution. Mixtures of buffers may be employed.

The manner in which the metal-organophosphorous ligand complex catalyst containing reaction fluid and aqueous buffer solution are contacted, as well as the amount of aqueous buffer solution, temperature, pressure and contact time are not narrowly critical and need only be sufficient to obtain the results desired. For instance, said treatment may be carried out in any suitable vessel or container, e.g. any vessel suitable for use as a liquid/liquid extractor, that provides a suitable means for thorough contact between the reaction fluid and the aqueous buffer solution. In general, it is preferred to pass the reaction fluid through the aqueous buffer solution in a sieve tray extractor column in a countercurrent fashion.

Contacting conditions may vary greatly and any suitable combination of such conditions may be employed herein. For instance, a decrease in one of such conditions may be compensated for by an increase in one or more of the other conditions, while the corollary is also true. In general, liquid temperatures ranging from 10° C. to 120° C., preferably from 20° C. to 80° C., and more preferably from 25° C. to 60° C., should be suitable for most instances, although lower or higher temperatures may be employed if desired. Advantageously, the treatment is carried out at pressures ranging from ambient to reaction pressure, and the contact time may vary from a matter of seconds or minutes to a few hours or more.

Success in removing phosphorus acidic compounds from the reaction fluid according to the subject invention may be determined by measuring the rate of degradation (consumption) of the organophosphorous ligand present in the hydroformylation reaction medium. The consumption rate can vary over a wide range, e.g., from <0.6 up to 5 grams per liter per day, and will be governed by the best compromise between cost of ligand and treatment frequency to keep hydrolysis below autocatalytic levels. Preferably, the aqueous buffer solution treatment is carried out in such a manner that the consumption of the desired organophosphorous ligand present in the hydroformylation reaction medium is maintained at an acceptable rate, e.g., <0.5 grams of ligand per liter per day, and more preferably <0.1 grams of ligand per liter per day, and most preferably <0.06 grams of ligand per liter per day. As the neutralization and extraction of phosphorus acidic compounds into the aqueous buffer solution proceeds, the pH of the buffer solution will slowly decrease.

The removal of at least some amount of phosphorus acidic compounds, for example, $H_3PO_3$, $H_3PO_4$, aldehyde acids such as hydroxy alkyl phosphonic acids, such as hydroxyl butyl phosphonic acid, hydroxyl pentyl phosphonic acid, and the like, from the hydroformylation system allows one to control the acidity of the hydroformylation reaction medium, thereby stabilizing the useful organophosphorous ligand by preventing or lessening its hydrolytic decomposition. The need to control the acidity in organophosphorous promoted metal catalyzed hydroformylation is explained herein. Thus, the purpose of the buffer is to remove or reduce excessive acidity from the catalyst system in order to maintain a proper acidity level in the reaction fluid so that the consumption of the useful organophosphorous ligands do not hydrolytically degrade at an unacceptable rate while keeping catalyst activity at a productive level. The best means for regulating such acidity is to extract (remove) such phosphorus acidic materials from the reaction fluid using an aqueous buffer solution. In this way the acidic materials are neutralized and extracted into the aqueous solution as disclosed herein as opposed to merely being scavenged and/or neutralized and allowed to remain in the reaction medium, thereby avoiding accumulation of such scavenged and/or neutralized by-products, and preventing further possible necessary secondary chemistry or the buildup of salt deposits in the reactor zone and/or separator zone. Said treatment of the metal-organophosphorous ligand complex catalyst containing reaction fluid with the aqueous buffer solution may be conducted in any suitable manner or fashion desired that does not unduly adversely affect the fundamental hydroformylation process from which said reaction fluid is derived. For instance, the aqueous buffer treatment may be conducted on all or any portion of the desired reaction fluid that is to be treated in at least one buffer treatment zone and that has been removed from the at least one reaction zone or the at least one separation zone. The treated reaction fluid may then be returned to the at least one reaction zone or the at least one separation zone. Alternatively, buffer solution may be sprayed into or otherwise added to the at least one reaction zone or the at least one separation zone to achieve acidity control. The aqueous buffer layer formed may then be separated, e.g., decanted, from the reaction fluid. As noted above, it is known that an aqueous buffer solution that becomes entrained in a hydroformylation reaction fluid containing a metal-organophosphorous ligand complex catalyst and that is transferred to the reaction zone does not result in an appreciable or significant increase in the formation of higher molecular weight aldehydes, e.g., dimers, trimers, etc.

The use of an aqueous buffer solution is especially adaptable for use in continuous liquid catalyst recycle hydroformylation processes that employ the invention of U.S. Pat. No. 5,288,918, which comprises carrying out the process in the presence of a catalytically active enhancing additive, said additive being selected from the class consisting of added water, a weakly acidic compound (e.g.; biphenol), or both added water and a weakly acidic compound. The enhancing additive is employed to help selectively hydrolyze and prevent the build-up of an undesirable monophosphite by-product that can be formed during certain processes and that poisons the metal catalyst as explained therein. Nonetheless, the preferred hydroformylation process of this invention is still considered to be essentially a "non-aqueous" process, which is to say, any water present in the hydroformylation reaction medium is not present in an amount sufficient to cause either the hydroformylation reaction or said medium to be considered as encompassing a separate aqueous or water phase or layer in addition to an organic phase; provided, however, that this limitation does not apply to the separation zones of the process.

In one embodiment of the invention, an aqueous buffer solution is introduced into the reaction zone and/or the separation zone in an amount sufficient to remove at least some amount of the phosphorus acidic compounds from said reaction fluid. Thus, for example, the aqueous buffer solution may be used to treat all or part of a reaction fluid of a continuous liquid catalyst recycle hydroformylation process that has been removed from the reaction zone at any time prior to or after separation of the aldehyde product therefrom. The preferred method of operation is to pass all or a portion of the reaction fluid, before or after aldehyde removal, through the aqueous buffer solution. Alternatively, buffer solution may be sprayed into or otherwise added to a reaction zone or a separation zone to achieve acidity control. The aqueous buffer layer formed may then be separated, e.g., decanted, from the reaction fluid. An advantage of this scheme is that neutralization capability is immediately available if acidity forms in the reaction fluid.

Optionally, an organic nitrogen compound may be added to the reaction fluid, e.g., hydroformylation reaction fluid in the reactor, to scavenge the acidic hydrolysis by-products formed upon hydrolysis of the organophosphorous ligand, as taught, for example, in U.S. Pat. No. 4,567,306. Such organic nitrogen compounds may be used to react with and to neutralize the acidic compounds by forming conversion product salts therewith, thereby preventing the metal, e.g., rhodium, from complexing with the acidic hydrolysis by-products and thus helping to protect the activity of the metal, e.g., rhodium, catalyst while it is present in the reaction zone under reaction, e.g., hydroformylation, conditions. The choice of the organic nitrogen compound for this function is, in part, dictated by the desirability of using a basic material that is soluble in the reaction medium and does not tend to catalyze the formation of aldols and other condensation products at a significant rate or to unduly react with the product, e.g., aldehyde.

Such organic nitrogen compounds may contain from 2 to 30 carbon atoms, and preferably from 2 to 24 carbon atoms. Primary amines should be excluded from use as said organic nitrogen compounds. Preferred organic nitrogen compounds should have a distribution coefficient that favors solubility in the organic phase. In general, more preferred organic nitrogen compounds useful for scavenging the phosphorus acidic compounds present in the reaction fluid of this invention include those having a pKa value within ±3 of the pH of the aqueous buffer solution employed. The pKa value of the organic nitrogen compound most preferably will be essentially about the same as the pH of the aqueous buffer solution employed. While it may be preferred to employ only one such organic nitrogen compound at a time in any given process, if desired, mixtures of two or more different organic nitrogen compounds may also be employed.

Illustrative organic nitrogen compounds include e.g., tri-alkylamines, such as triethylamine, tri-n-propylamine, tri-n-butylamine, tri-iso-butylamine, tri-iso-propylamine, tri-n-hexylamine, tri-n-octylamine, dimethyl-iso-propylamine, dimethyl-hexadecylamine, methyl-di-n-octylamine, and the like, as well as substituted derivatives thereof containing one or more noninterfering substituents such as hydroxy groups, for example triethanolamine, N-methyl-di-ethanolamine, tris-(3-hydroxypropyl)-amine, and the like. Heterocyclic amines can also be used such as pyridine, picolines, lutidines, collidines, N-methylpiperidine, N-methylmorpholine, N-2'-hydroxyethylmorpholine, quinoline, iso-quinoline, quinoxaline, acridien, quinuclidine, as well as, diazoles, triazole, diazine and triazine compounds, and the like. Also suitable for possible use are aromatic tertiary amines, such as N,N-dimethylaniline, N,N-diethylaniline, N,N-dimethyl-p-toluidine, N-methyldiphenylamine, N,N-dimethylbenzylamine, N,N-dimethyl-1-naphthylamine, and the like. Compounds containing two or more amino groups, such as N,N,N',N'-tetramethylethylene diamine and triethylene diamine (i.e. 1,4-diazabicyclo-[2,2,2]-octane) can also be mentioned.

Preferred organic nitrogen compounds useful for scavenging the phosphorus acidic compounds present in the reaction fluids of the this invention are heterocyclic compounds selected from the group consisting of diazoles, triazoles, diazines and triazines, such as those disclosed and employed in U.S. Pat. No. 5,731,472. For example, benzimidazole and benztriazole are preferred candidates for such use.

The amount of organic nitrogen compound that may be present in the reaction fluid for scavenging the phosphorus acidic compounds present in the reaction fluids of the this invention is typically sufficient to provide a concentration of at least 0.0001 moles of free organic nitrogen compound per liter of reaction fluid. In general, the ratio of organic nitrogen compound to total organophosphorous ligand (whether bound with rhodium or present as free organophosphorous ligand) is at least 0.1:1 and even more preferably at least 0.5:1. The upper limit on the amount of organic nitrogen compound employed is governed mainly only by economical considerations. Organic nitrogen compound: organophosphorous ligand molar ratios of at least 1:1 up to 5:1 should be sufficient for most purposes.

It is to be understood that the organic nitrogen compound employed to scavenge said phosphorus acidic compounds need not be the same as the heterocyclic nitrogen compound employed to protect the metal catalyst under harsh conditions such as exist in the product, e.g., aldehyde, vaporizer-separator, as taught in U.S. Pat. No. 5,731,472. However, if said organic nitrogen compound and said heterocyclic nitrogen compound are desired to be the same and perform both said functions in a given process, care should be taken to see that there will be a sufficient amount of the heterocyclic nitrogen compound present in the reaction medium to also provide that amount of free heterocyclic nitrogen compound in the process, e.g., hydroformylation vaporizer-separator, that will allow both desired functions to be achieved.

Accordingly, the aqueous buffer solution treatment will not only remove free phosphoric acidic compounds from the metal-organophosphorous ligand complex catalyst containing reaction fluids, the aqueous buffer solution also surprisingly removes the phosphorus acidic material of the conversion product salt formed by the use of the organic nitrogen compound scavenger when employed, i.e., the phosphorus acid of said conversion product salt remains behind in the aqueous buffer solution, while the treated reaction fluid, along with the reactivated (free) organic nitrogen compound is returned to the reaction zone.

Thus, deactivation is minimized or prevented by the addition of a free heterocyclic nitrogen compound having a five or six membered heterocyclic ring consisting of 2 to 5 carbon atoms and from 2 to 3 nitrogen atoms, at least one of said nitrogen atoms containing a double bond. Such free heterocyclic nitrogen compounds may be selected from the class consisting of diazole, triazole, diazine, and triazine compounds, such as, e.g., benzimidazole or benzotriazole, and the like. The term "free" as it applies to said heterocyclic nitrogen compounds is employed therein to exclude any acid salts of such heterocyclic nitrogen compounds, i.e., salt compounds formed by the reaction of any phosphorus acidic compound present in the reaction fluid with such free heterocyclic nitrogen compounds as discussed herein above.

It is to be understood that while it may be preferred to employ only one free heterocyclic nitrogen compound at a time in any given process, if desired, mixtures of two or more different free heterocyclic nitrogen compounds may also be employed in any given process. Moreover the amount of such free heterocyclic nitrogen compounds present during harsh conditions, e.g., the vaporization procedure, need only be that minimum amount necessary to furnish the basis for at least some minimization of such catalyst deactivation as might be found to occur as a result of carrying out an identical metal catalyzed liquid recycle hydroformylation process under essentially the same conditions, in the absence of any free heterocyclic nitrogen compound during vaporization separation of the aldehyde product. Amounts of such free heterocyclic nitrogen compounds ranging from 0.01 up to 10 weight percent, or higher if desired, based on the total weight of the reaction fluid to be distilled should be sufficient for most purposes.

The reaction fluid to be treated with the aqueous buffer solution may contain, in addition to the metal-organophosphorous ligand complex catalyst and its organic solvent, the aldehyde product, free organophosphorous ligand, unreacted olefin, and any other ingredient or additive consistent with the reaction medium of the hydroformylation process from which said reaction fluids are derived.

Moreover, removal of the desired aldehyde product can cause concentrations of the other ingredients of the reaction fluid to be increased proportionately. Thus, for example, the organophosphorous ligand concentration in the reaction fluid to be treated by the aqueous buffer in accordance with the process of this invention may range from between 0.005 and 15 weight percent based on the total weight of the reaction fluid. Preferably the ligand concentration is between 0.01 and 10 weight percent, and more preferably is between 0.05 and 5 weight percent on that basis. Similarly, the concentration of the metal in the metal-organophosphorous ligand complex catalyst containing reaction fluid to be treated by the aqueous buffer in accordance with the process of this invention may be as high as 5000 ppmw based on the weight of the reaction fluid. Preferably the metal concentration is between 50 and 2500 ppmw based on the weight of the reaction fluid, and more preferably is between 70 and 2000 ppmw.

The hydroformylation processes of this invention may be asymmetric or non-asymmetric, the preferred processes being non-asymmetric, and may be conducted in any continuous or semi-continuous fashion and may involve any catalyst liquid and/or gas recycle operation desired. Thus, it should be clear that the particular hydroformylation process for producing such aldehydes from an olefinic unsaturated compound, as well as the reaction conditions and ingredients of the hydroformylation process are not critical features of this invention.

The recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. No. 5,430,194 and U.S. Pat. No. 5,681,473, or by the more conventional and preferred method of distilling it, i.e. vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydroformylation reaction fluid employable herein includes any fluid derived from any corresponding hydroformylation process that contains at least some amount of four different main ingredients or components, i.e., the aldehyde product, a metal-organophosphorous ligand complex catalyst, free organophosphorous ligand and an organic solubilizing agent for said catalyst and said free ligand, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those that have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation processes encompassed by this invention may include any suitable type hydroformylation conditions heretofore employed for producing optically active and/or non-optically active aldehydes. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominately by the amount of reactants necessary to obtain a desired rate of reaction. More specifically the carbon monoxide partial pressure of the hydroformylation process of this invention is preferably from 1 to 6,900 kPa, and more preferably from 21 to 5,500 kPa, while the hydrogen partial pressure is preferably from 34 to 3,400 kPa and more preferably from 69 to 2,100 kPa. In general, $H_2$:CO molar ratio of gaseous hydrogen to carbon monoxide may range from 1:10 to 100:1 or higher, the more preferred hydrogen to carbon monoxide molar ratio being from 1:10 to 10:1.

In general, the hydroformylation process may be conducted at any operable reaction temperature. Advantageously, the hydroformylation process is conducted at a reaction temperature from −25° C. to 200° C. In general, hydroformylation reaction temperatures of 50° C. to 120° C. are preferred for all types of olefinic starting materials. When non-optically active aldehyde products are desired, achiral type olefin starting materials and organophosphorous ligands are employed and when optically active aldehyde products are desired prochiral or chiral type olefin starting materials and organophosphorous ligands are employed. The hydroformylation reaction conditions employed will be governed by the type of aldehyde product desired, as is known by those skilled in the art.

The hydroformylation processes of this invention may be carried out using one or more suitable reactors such as, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. The reaction zone employed in this invention may be a single vessel or may comprise two or more discrete vessels. The separation zone employed in this invention may be a single vessel or may comprise two or more discrete vessels. The buffer treatment zone employed in this invention may be a single vessel or may comprise two or more discreet vessels. It should be understood that the reaction zone(s) and separation zone(s) employed herein may exist in the same vessel or in different vessels. For example, reactive separation techniques such as reactive distillation, reactive membrane separation and the like may occur in the reaction zone(s).

The hydroformylation processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be substantially inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The hydroformylation processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation processes of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation processes useful in this invention may be carried out in a multistaged reactor such as described, for example, in U.S. Pat. No. 5,728,893. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Using fewer vessels reduces the overall capital and maintenance required.

As indicated above, it is generally preferred to carry out the hydroformylation processes of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-organophosphorous ligand complex catalyst, and free organophosphorous ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process of this invention comprises a continuous liquid catalyst recycle process. Suitable liquid catalyst recycle procedures are disclosed, for example, in U.S. Pat. Nos. 4,668,651; 4,774,361; 5,102,505 and 5,110,990.

In one embodiment of this invention, the aldehyde product mixtures may be separated from the other components of the crude reaction mixtures in which the aldehyde mixtures are produced by any suitable method. Suitable separation methods include, for example, solvent extraction, crystallization, distillation, vaporization, wiped film evaporation, falling film evaporation, phase separation, filtration and the like. It may be desired to remove the aldehyde products from the crude reaction mixture as they are formed through the use of trapping agents as described in WO 88/08835. One method for separating the aldehyde mixtures from the other components of the crude reaction mixtures is by membrane separation. Such membrane separation can be achieved as set out in U.S. Pat. Nos. 5,430,194 and 5,681,473.

As indicated above, at the conclusion of (or during) the process of this invention, the desired aldehydes may be recovered from the reaction mixtures used in the process of this invention. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorous ligand and reaction products. When an alpha-mono-olefin reactant is also employed, the aldehyde derivative thereof can also be separated by the above methods.

More particularly, distillation and separation of the desired aldehyde product from the metal-organophosphorous complex catalyst containing reaction fluid may take place at any suitable temperature desired. In general, it is recommended that such distillation take place at relatively low temperatures, such as below 150° C., and more preferably at a temperature in the range of from 50° C. to 140° C. It is also generally recommended that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g. vaporizer/separator, wherein the desired aldehyde product is distilled. In general, distillation pressures ranging from vacuum pressures on up to total gas pressure of 340 kPa should be sufficient for most purposes.

Illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(p-thienoylphenyl)propionaldehyde, S-2-(3-fluoro-4-phenyl)phenylpropionaldehyde, S-2-[4-(1, 3-dihydro-1-oxo-2H-isoindol-2-yl)phenyl]propionaldehyde, S-2-(2-methylacetaldehyde)-5-benzoylthiophene and the like.

SPECIFIC EMBODIMENTS OF THE INVENTION

All parts and percentages in the following examples are by weight unless otherwise indicated. Pressures are given as absolute pressure unless otherwise indicated.

General Procedure

A liquid recycle reactor system is employed that consists of three 1 liter stainless steel stirred tank reactors connected in series. Each reactor is equipped with a vertically mounted agitator and a circular tubular sparger located near the bottom of the reactor. Each sparger contains a plurality of holes of sufficient size to provide the desired gas flow into the liquid body in the reactor. The spargers are used for feeding the olefin and/or syngas to the reactor, and can also be used to introduce unreacted gases to each reactor. Each reactor has a silicone oil shell as a means of controlling reactor temperature. Reactors 1 to 2 and reactors 2 to 3 are further connected via lines to transfer any unreacted gases and lines to allow a portion of the liquid solution containing aldehyde product and catalyst to be pumped from reactor 1 to reactor 2 and from reactor 2 to reactor 3. Hence, the unreacted olefin of reactor 1 is further hydroformylated in reactor 2 and subsequently reactor 3. Each reactor also contains a pneumatic liquid level controller for maintaining the desired liquid level. Reactor 3 has a blow-off vent for removal of unreacted gases.

A portion of the liquid reaction solution is continuously pumped from Reactor 3 to a vaporizer, which consists of a heated vessel at reduced pressure. The effluent stream from the vaporizer is sent to a separator gas-liquid separator located at the bottom of the vaporizer, where vaporized aldehyde is separated from the non-volatile components of the liquid reaction solution. The vaporized aldehyde product is condensed and collected in a product receiver. A pneumatic liquid level controller controls the desired non-volatile component level, including catalyst to be recycled, at the bottom of the separator. The separator is connected to the buffer treatment vessel by a recycle line.

The non-volatile components, including catalyst to be recycled, from the separator are passed into the bottom of an aqueous buffer treatment packed column, which consists of a contacting region and a phase separation zone. Following the buffer treatment, the organic non-volatile layer, which contains catalyst to be recycled, is pumped from the phase separation zone through a recycle line into Reactor 1.

Comparative Experiment 1

Use of Sodium Phosphate Buffer (Not an Embodiment of the Invention)

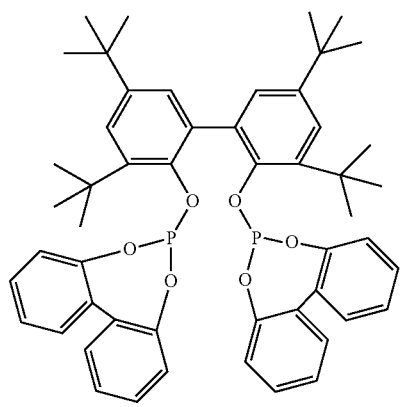

Ligand A

The hydroformylation reaction is conducted using the General Procedure described above. The reactor system is charged with 3-liters of catalyst solution comprising rhodium dicarbonyl acetylacetonate (75 ppm rhodium), Ligand A (0.15 wt %; 2.5 mole equivalents per mole rhodium), tetraethylene glycol dimethyl ether (15% by weight) and mixed $C_4$ aldehyde (85% by weight: n-butyraldehyde to iso-butyraldehyde ratio of 30:1). The reactors are then heated to 70° C. under flowing carbon monoxide and hydrogen. Reactor 1, 2 and 3 pressures are maintained at 130, 110, and 90 psig respectively. Propylene is fed to Reactor 1 at a rate of 1.8 gram moles per liter of reactor volume per hour. The vaporizer system is operated at 3 to 8 psig and 96 to 100° C.

The buffer treatment column is filled with 0.4M sodium phosphate in water. Each fresh buffer charge exhibits an initial pH of 7. The pH is carefully monitored, and the buffer is replaced when the pH declines to below 6.5.

Example 2

Use of Sodium Maleate Buffer

The hydroformylation reaction is conducted as described in Comparative Experiment 1, except that the buffer treatment is 0.4M sodium maleate for the first 65 days and 0.2M sodium maleate for the last 78 days at pH 7. The results of Comparative Experiment 1 and Example 2 are shown in Table 1.

TABLE 1

Comparison of sodium phosphate and sodium maleate

|  | Comparative Experiment 1 | Example 2 |
| --- | --- | --- |
| Run length (days) | 112 | 143 |
| Average HBPA capacity at pH = 6.5 change-out (ppm) | 340 | 790 |
| Number of fresh buffer charges required | 10 | 6 |
| Cumulative Ligand A usage (g/L/day) | 0.026 | 0.036 |

TABLE 1-continued

Comparison of sodium phosphate and sodium maleate

|  | Comparative Experiment 1 | Example 2 |
| --- | --- | --- |
| Sodium detected in recycled catalyst solution (ppm by atomic absorption) | <10 | <25 |
| Rhodium detected in aqueous buffer (ppm by atomic absorption) | <0.10 | <0.10 |

Hydroxyl butyl phosphonic acid (HBPA) is an ultimate acidic by-product of Ligand A decomposition. The data indicate an increased capacity of the sodium maleate buffer for HBPA, thus requiring less frequent buffer replacement while buffering in the desired pH range. Comparable ligand usage rates are observed, within experimental variability. The demonstration runs exhibit practically identical heavies formation rates in the normal range of the Ligand A performance Additional analysis that is performed during the course of the runs shows no new $^{31}P$ NMR resonances present in the catalyst solution as a result of the maleate buffer. Operationally, there is no change in the aldehyde/aqueous phase separation in the aqueous treatment zone. There is no detectable maleate ion observable in the organic catalyst fluid (by ion chromatography, detection limit 0.1 ppm). Thus, maleate buffer exhibits a greater buffering capacity over the desired range with essentially no detrimental effects on the catalyst solution.

Unexpectedly, no increased ligand loss was observed. This is surprising in view of the fact that maleic acid is a highly activated α,β-unsaturated carboxylic acid capable of Michael addition-type reactivity not normally associated with any of the prior art buffers, and, as such, practitioners of the art would avoid the continuous addition of such an apparently reactive reagent to their system. It is unexpected that hydroformylation catalysts comprised of rhodium and phosphites are not adversely affected by contact with maleate. It is also unexpected that maleate-type organic buffers give excellent acidity control with no loss of catalytic activity or ligand degradation due to Michael-type reactions.

What is claimed is:

1. A process comprising contacting a reaction fluid containing (a) a phosphorus acidic compound, (b) a metal-organophosphorus ligand complex catalyst that comprises a metal of Group 8, 9 or 10 complexed with an organophosphorous ligand, and, optionally, (c) free organophosphorus ligand, with an aqueous buffer solution to neutralize at least some amount of the phosphorus acidic compound of said reaction fluid to form a neutralized phosphorus acidic compound, wherein the buffer solution comprises a salt of an unsaturated aliphatic carboxylic acid represented by the formula:

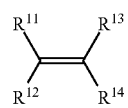

wherein $R^{11}$ to $R^{14}$ are hydrogen, —COOM, alkyl and cycloalkyl that contain from 1 to 24 carbon atoms and wherein at least one of $R^{11}$ and $R^{12}$ is a —COOM moiety and at least one of $R^{13}$ and $R^{14}$ is a —COOM moiety, wherein the concentration of the salt in the buffer solution is from 0.001M to 0.8M and wherein the pH of the buffer solution is from 6 to 8.

2. The process of claim 1 wherein the unsaturated aliphatic carboxylic acid comprises at least one dicarboxylic acid.

3. The process of claim 2 wherein the salt comprises at least one maleate or fumarate salt.

4. The process of claim 3 wherein the salt comprises at least one maleate salt.

5. The process of claim 1 wherein M is selected from the group consisting of sodium, potassium and calcium.

6. The process of claim 1 wherein the concentration of the salt in the buffer solution is from 0.01 to 0.04M.

7. The process of claim 1 wherein the contacting is done in a countercurrent manner.

8. The process of claim 1 wherein the reaction fluid comprises an organic phase and the buffer solution comprises an aqueous phase.

9. The process of claim 1 wherein the neutralized phosphorus acidic compound is separated from the process.

* * * * *